United States Patent [19]

Piper et al.

[11] 4,322,279

[45] Mar. 30, 1982

[54] ELECTRODE ARRANGEMENTS

[75] Inventors: Phillip G. Piper, Millhaugh-by-Methven; John P. Rutzen, Perthshire, both of Scotland

[73] Assignee: G. R. International Electronics Limited, Great Britain

[21] Appl. No.: 195,914

[22] Filed: Oct. 10, 1980

[51] Int. Cl.³ .................... C12M 1/34; C12Q 1/70; G01N 27/30

[52] U.S. Cl. .................... 204/195 B; 204/1 T; 23/230 B; 435/291

[58] Field of Search .................... 204/195 B, 1 T; 23/230 B; 435/5, 34, 291, 288, 871

[56] References Cited

U.S. PATENT DOCUMENTS

| | | | |
|---|---|---|---|
| 3,403,081 | 9/1968 | Rohrback et al. | 435/291 |
| 3,743,581 | 7/1973 | Cady et al. | 435/291 |
| 3,868,223 | 2/1975 | Robock et al. | 204/195 B |
| 4,020,830 | 5/1977 | Johnson et al. | 204/195 B |
| 4,172,770 | 10/1979 | Semersky et al. | 435/291 |
| 4,200,293 | 4/1980 | Wilkins et al. | 435/291 |

*Primary Examiner*—Arthur C. Prescott
*Attorney, Agent, or Firm*—William A. Drucker

[57] ABSTRACT

A bacterial activity sensing electrode or probe comprises an insulating substrate carrying a conductive pattern as two conductors as a mask-produced thick film. The conductors terminate in bare sensor parts and also in bare connection parts and are otherwise covered by an insulating coating also mask-produced. The substrate has a molded-on cap of suitably inert plastics material to fit directly to a sample bottle with the sensor parts inside and the connector parts offset to one side for making a push-bit electrical connection thereto. Inoculation of a growth medium is via a through-passage in the cap and ruptuable means associated therewith.

10 Claims, 3 Drawing Figures

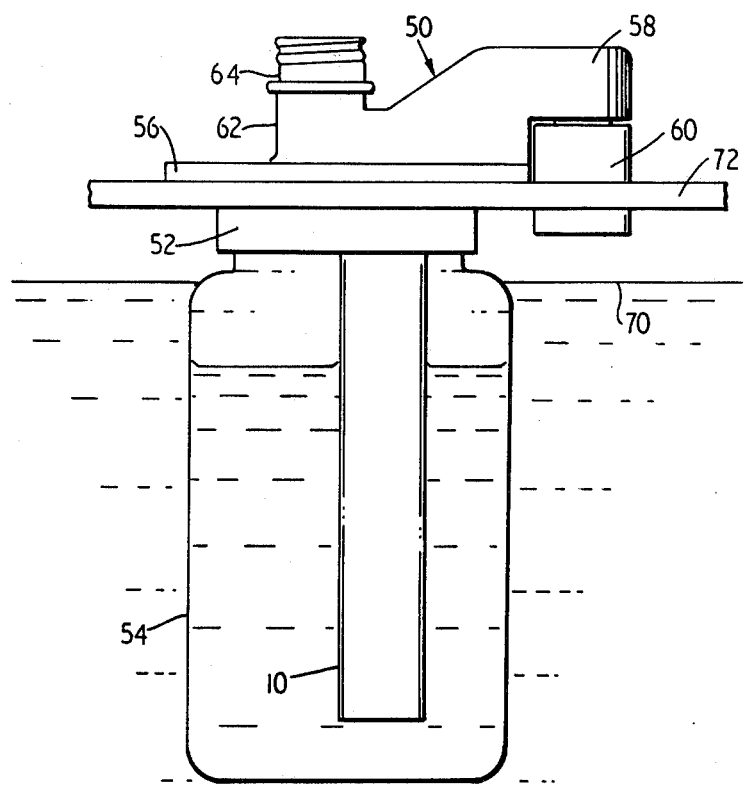
—FIG.3—

ELECTRODE ARRANGEMENTS

The invention relates to electrodes and has particular reference to the electrical sensing of bacterial activity in samples thereof, usually in a variety of media and/or concentrations of medium.

Prior proposals for sensing electrical parameters of inoculated media samples to test for bacterial growth therein have tended to suggest electrodes that are somewhat impractical as to their economic manufacture on a reasonable scale. Thus, actually wiring through a sample container of or to platinum electrodes has been suggested, which is not easy to do on a basis of high accuracy and ready repeatability as is required for a system in which a large number of samples are to be simultaneously monitored, especially if they are to be compared one with another over a period of time. Sheathed insulations also give rise to problems of toxicity, autoclaving, and adherence to metal probes.

It is an object of this invention to provide an electrode device that can be produced reliably to a high accuracy and is readily fitted to a sample container.

To this end, we propose that a conductive composition, preferably of noble metal, be laid down in a predetermined pattern on a non-metallic surface or substrate using mask techniques, and that satisfies repeatability of production at high accuracy, reasonable cost and volume, as, for example, previously proved in relation to manufacture of thick film electronic circuits.

The use of a noble metal pattern on an insulating substrate or surface avoids problems inherent in noble metal plating of a base metal which we have found to give rise to electrical noise due, we believe, to electrical activity in plating micropores, most especially when in a liquid medium that may act as an electrolyte. Similar problems arise with tipped electrodes where intermetallic interfaces or junctions come into contact with a liquid medium being tested. We therefore prefer to avoid such interfaces or junctions, especially when, as is preferred herein, the electrical parameter to be sensed is resistance or conductance.

Also, the substrate is readily provided with a configuration suitable for mounting in, on or by a sample container cap, stopper or the like, preferably and advantageously by moulding-in, which again improves achievement of repeatable accuracy.

Further use can be made of mask application techniques for ensuring exposure only of prescribed parts of the conductor pattern. Thus, an electrically insulating layer can be laid down over at least other parts of the conductor pattern. A crystallizable glass dielectric is preferred as an overglaze and may be fired in a furnace after deposition by screen printing as an ink in a manner analagous to that preferred for conductor pattern deposition.

We particularly envisage a substrate, carrying a conductor pattern and selective overglaze, locked in a moulded, preferably moulded-on, container cap with two ends or edges of the substrate protruding, one into a said container and the other outside a said container, and both having exposed conductor pattern to sense conductivity/resistance of container contents, and interconnect with appropriate detection circuitry, respectively, the latter conveniently via an edge connector of or for a tray or holder for containers.

One embodiment of the invention will now be described, by way of example with reference to the accompanying drawings, in which:

FIG. 3 shows a sample bottle fitted in a bath.

Figure 1:
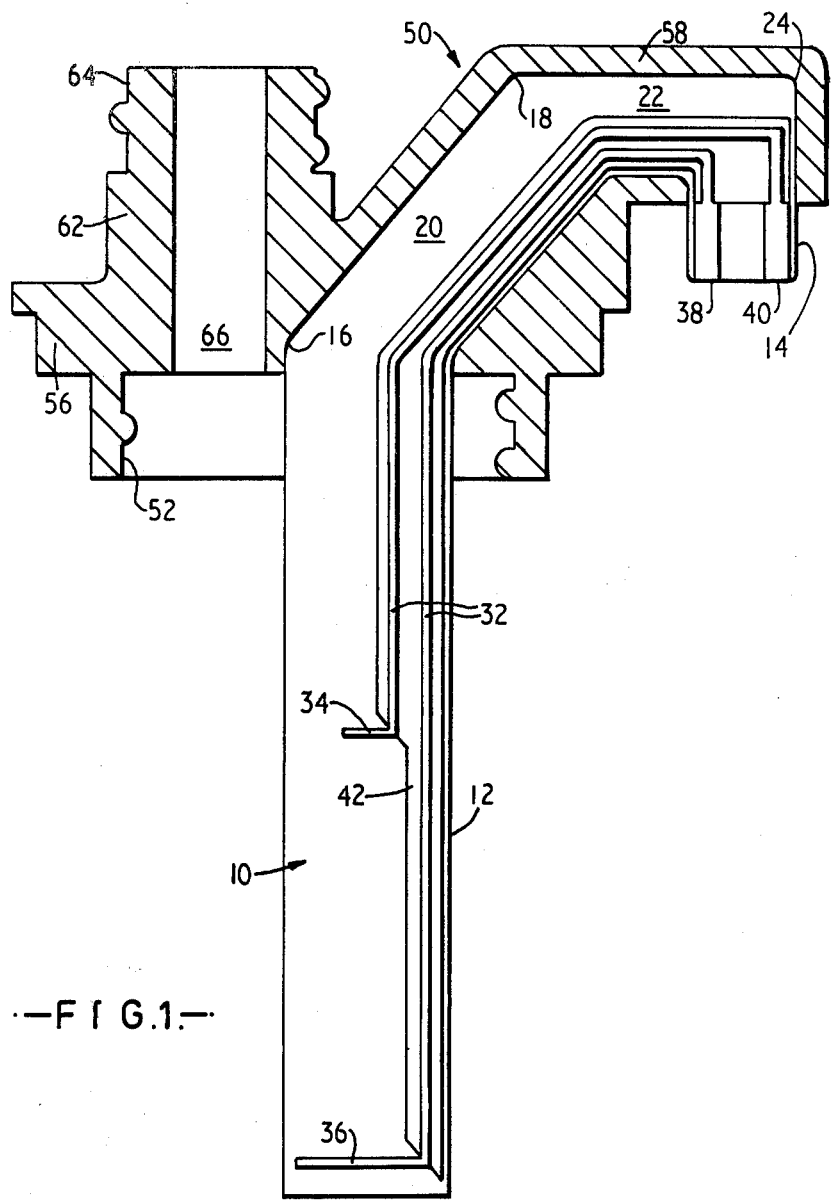
FIG. 1 is a sectional view through a cap carrying an electrode hereof.
Figure 2:
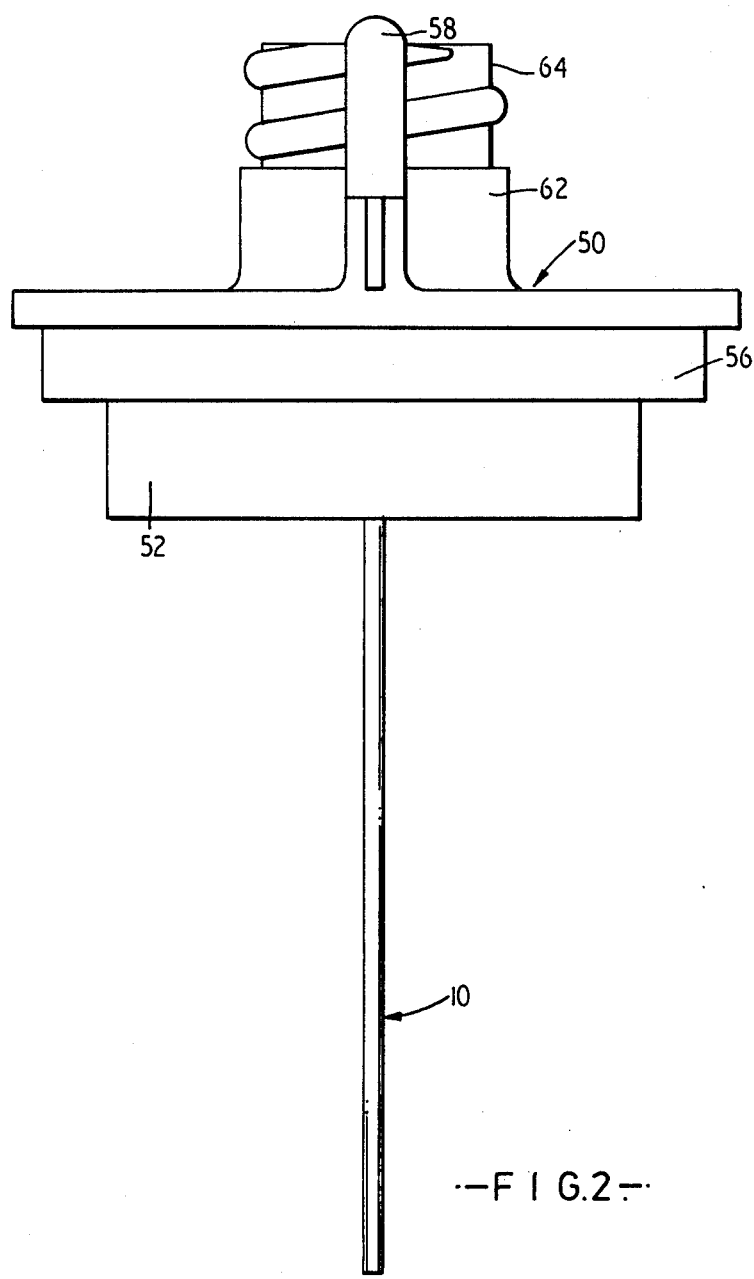
FIG. 2 is a view at right angles to the section of FIG. 1.

In the drawings, an electrode comprises a flat ceramic substrate 10, conveniently having a high alumina content and capable of withstanding firing temperatures of 1000° C. or more. Normally, ceramic substrates will be between 0.6 and 1.5 mm thick, preferably 0.8 to 1.2 mm thick, to give a satisfactorily robust but compact probe portion 12 of a convenient width, such as 10 to 20 mm, to suit a bacterial growth sample bottle.

The substrate 10 is shown in plan as having one end 14 offset from the probe portion 12 and returned to substantial parallelism therewith. This particularly facilitates insertion of the end 14 as a push fit into an electrical connector, see FIG. 3. The offsetting is shown achieved by two successive bends 16, 18 producing a portion 20 angled obliquely to the probe portion and a portion 22 at right angles to the probe portion, followed by a right angle bend 24, an arrangement that is particularly well suited to incorporation in a cap as will become apparent.

The substrate has on one of its major surfaces a pattern 32 of conductive material laid down as a thick film, conveniently by screen printing of a gold ink through a stainless steel mesh rendered selectively blocked and open by impregnation with a material rendered water insoluble by exposure to ultra-violet light according to a pattern desired by photographic reduction from a many times larger master, and washing out unexposed material. Any steel mesh size that gives continuous electrical conductivity may be used, and the gold ink may be Engelhard T4474, the process advantageously resulting in a deposited layer of from 15 to 25 microns thick. Conductor resistance is not considered to be critical in itself so long as it is consistently reproduced but 0.05 ohms per square after firing has been found to be suitable. Firing with a gold conductor usually produces a thickness reduction of about 25%.

All but prescribed sensor 34, 36 and connector 38, 40 parts of the conductor pattern are indicated as being insulated by a coating 42, preferably of a crystallizable glass dielectric, also available commercially as an ink, and screen printed over the conductive pattern to give complete coverage of the underlying conductive material. It will be appreciated that the locations, shapes and sizes of the free sensor parts 34, 36 of the conductor pattern are thus readily determined to very high accuracy, much higher than could be achieved by conventional sheath insulation over conductor wires that might become bent or have their insulation pulled back stripped or frayed inadvertently or be subject to differential effects of their immediate environments.

The double printed ceramic substrate is dried and then fired to render its coating permanently affixed. This is preferably done in a controlled manner using a through-pass furnace having a carefully controlled temperature profile along the path of the substrate in accordance with ink manufacturer's specifications and separately from or together with conductive pattern firing as desired, recommended or necessary.

The probe so formed will have no noble metal-to-base metal interfacing and noise levels will be low in the intended operation, especially for the smooth continuous surfaces obtainable with ceramic substrates. Instead of high alumina ceramics, silica ceramics or glasses could be used, or a base metal substrate with a non-metallic coating, for example a steel strip coated with porcelain or even enamelled.

There are substantial advantages compared with sleeve insulated probes as there is no tendency for sleeving to contract on autoclaving and thus expose a junction between base metal and a noble metal tip, which would normally be the only economically acceptable construction. Also, and perhaps even more importantly, there are severe problems in finding suitable plastics material for sleeving because of the multiple requirements of adhesion to metal, autoclavability, and non-toxicity.

The resulting probe is shown in a cap 50 of moulded-on plastics material that is inert for the growth media and products of bacteria growth tests to be performed. The cap 50 has an internally screwed neck 52 to facilitate sealed fitting thereto of a sample bottle 54 with an exteriorly threaded neck. Screw fitting is preferred to push-fitting for ease of sealing but that latter might be used if desired.

We particularly envisage that the preferred moulding-on of the cap 50 will be done by transfer moulding as is known in epoxy based encapsulation of hybrid electrical/electronic circuits. Suitable substantially non-toxic materials are available commercially from Emerson & Cunnings (Ecomold 4120) and Hysal (MG 17F). Conventional injection moulding of materials such as polypropylenes or polycarbonates is also envisaged. Then, there may be problems of ensuring bacteria-tight sealing to the probe, such may be overcome by the use of a seal material, for example of room temperature welcoming synthetic rubber as a primer on the probe or as a seal "ring" moulded thereon at the position of its intended protrusion from the cap into a sample bottle obtaining a bacteria-tight seal to the sample bottle may also be aided by a laid-in seal of similar material at least about the position of the sample bottle rim.

Bacteria-tight sealing is important not only because samples to be tested may include dangerous pathogens, but also as cross-infections can otherwise result between sample bottles in an array thereof. Furthermore, the injection of blood samples into culture media already contained in sample bottles can produce a significant temporary pressure increase just when the bacteria are at their most concentrated.

One other possible construction of cap and probe is mentioned as we have used it successfully for our prototypes. This is to use a ready moulded or fabricated cap with a slot into which a probe can be push-fitted. Then one-or-two part seatant materials, such as of synthetic rubber, substantially inert to the products of bacterial activity, may be applied as coatings and/or seal mouldings on the probe.

Above its neck 52, the cap 50 has an enlarged head 56 with a side extension 58 encapsulating the bends 16, 18 24 of the probe but leaving its end 14 free for push fitting onto an edge connector, 60 in FIG. 3. At one side of the extension 58 the cap 50 has an upstanding entry provision 62 externally threaded at its free end 64 to enable closure of its through passage 66 extending directly downwardly into an attached bottle. This bore 66 will usually have a rupturable diaphragm for a hypodermic needle or other inocculator of growth medium in the bottle. That diaphragm may possibly be a thinned part of the moulding, or an attached frangible, but is preferably a self-sealing piercable film or sheet.

The entire probe and cap unit is autoclavable for sterilisation purposes and will normally, and most conveniently, be fitted to a sample bottle 54 prior to fitment as shown in FIG. 3 in a temperature controlled bath of water 70 via a tray 72. The tray 72 will usually be apertured to hold a plurality of sample bottles, for example 32 in a 4×8 matrix array and, for each row of bottles will have a multiple entry edge connector each entry of which will be located to register with a different probe end 14 of the caps on the sample bottles. Clearly, individual electrical connectors could be provided, one for each bottle position.

As shown, the bottle cap 50 has a double ledge formation 80, 82 so that its part between the ledges will fit neatly in the tray 72, preferably as a push fit and the tray itself can then serve as a top closure of the water bath and thus assist in containing and accurately controlling the heat of the water itself to very close tolerances.

In general probe/cap assemblies or units hereof are robust and will withstand normal sterilisation and cleaning processes without developing leaks.

We have mentioned noble metals as conductors and platinum or gold are satisfactory inert, stable and non-toxic for our intended use. However, silver might have to be plated with gold or platinum to ensure that it was not attached or did not reach with the products of bacterial activity.

We claim:

1. Bacterial activity sensing electrode assembly for a bacterial testing container, comprising electrically conductive material laid down by thick film techniques in a predetermined pattern on a non-metallic surface using a mask, and having no metal-to-metal interfaces, such surface being on a probe carrying a cap or stopper between its bacterial sensing surface and electrode connection means.

2. A bacterial activity sensing electrode according to claim 1, wherein the conductive material is a noble metal.

3. A bacterial activity sensing electrode according to claim 2, comprising an electrically insulating layer laid over parts of the conductive material so as to expose only other prescribed parts of the conductive pattern.

4. A bacterial activity sensing electrode according to claim 3, wherein the electrically insulating layer is a crysallisable glass dielectric.

5. A bacterial activity sensing electrode according to claim 4, wherein the glass dielectric comprises a screen printed ink layer fired in a furnace.

6. A bacterial activity sensing electrode according to any preceding claim, wherein the non-metallic surface is of an insulating ceramic substrate constituting said probe.

7. A bacterial activity sensing electrode according to claim 6, wherein the substrate has a configuration presenting a portion offset or bent from the part to enter the container and the cap or stopper is present as a moulding formed in-situ on said portion.

8. A bacterial activity sensing electrode according to claim 7, wherein two conductive strips extend from an end at or adjacent said portion to different positions along said part in the direction of the depth of a said container.

9. A bacterial activity sensing electrode according to claim 8, wherein said strips are bare at said positions and also at said end where they offer purchase for a push-fit electrical connection device.

10. A bacterial activity sensing electrode according to claim 9, wherein said end protrudes from said cap or stopper moulding and is returned to substantial parallelism with the substrate part to enter the container.

* * * * *